United States Patent [19]

Shiga et al.

[11] Patent Number: 4,517,982
[45] Date of Patent: May 21, 1985

[54] SENSING DEVICE FOR CARDIO-PULMONARY FUNCTIONS

[75] Inventors: Tetsuya Shiga; Shinichi Okawa; Kenichi Yoshida; Junichi Hiramoto, all of Osaka, Japan

[73] Assignee: Sumitomo Electric Industries, Ltd., Osaka, Japan

[21] Appl. No.: 406,145

[22] Filed: Aug. 9, 1982

[30] Foreign Application Priority Data

Aug. 10, 1981 [JP] Japan ................... 56-124180

[51] Int. Cl.³ .................. A61B 5/00; A61B 5/04; A61B 5/08
[52] U.S. Cl. .................. 128/635; 128/639; 128/671; 128/700
[58] Field of Search .................. 128/635, 639–641, 128/670, 671, 716, 700

[56] References Cited

U.S. PATENT DOCUMENTS 4,265,250 5/1981 Parker .................. 128/635
4,294,258 10/1981 Bernard .................. 128/635
4,320,764 3/1982 Hon .................. 128/635

FOREIGN PATENT DOCUMENTS 2930663 2/1981 Fed. Rep. of Germany ...... 128/635

OTHER PUBLICATIONS

Knight et al., "Monitoring the Respiratory and Heart Rate . . . ", Med. & Biol., Eng. & Comp., Nov. 1900, pp. 797–798.

Primary Examiner—Lee S. Cohen
Attorney, Agent, or Firm—Sughrue, Mion, Zinn, Macpeak & Seas

[57] ABSTRACT

A sensor for use in detecting cardiopulmonary functions employs a skin-heating conductive surface for use in achieving vasodilitation for the measurement of $PO_2$ and $PCO_2$. The same surface is employed as an electrode for a heartbeat and/or respiration rate measuring device.

7 Claims, 3 Drawing Figures

SENSING DEVICE FOR CARDIO-PULMONARY FUNCTIONS

BACKGROUND OF THE INVENTION

The present invention encompasses sensing means for monitoring the cardio-pulmonary functions of a patient, especially new born babies in an intensive care unit. According to the present invention up to four functions or parameters; $PO_2$, $PCO_2$, the respiration rate and encardiography are measured in both a simultaneous and transcutaneous way. Among the above four functions the first two are relatively new while the latter items have been practiced for a long time.

As is generally known, the respiration rate and encardiography are measured such that two electrodes 2, 2' are applied to predetermined portions on the skin of the human subject 1 and fluctuations in the potential between the electrodes are taken as a measure of encardiography, while fluctuations in the impedance between these electrodes are used to measure the respiration rate. Referring to FIG. 1, signals related to the two mentioned functions are led to a resistor R, and signals related to the heartbeat (of low frequency) are taken out by means of a low-pass filter 3 connected across the resistor R, while an alternate source of 50 kHz supplied for measurement is taken out by means of a tuning circuit 4 and detected in order to measure the respiration rate. Accordingly, two electrodes must be applied to the surface of the human body.

In addition, the transcutaneous measurement of $PO_2$ and $PCO_2$ require the attachment of a $PO_2$ sensitive polarographic sensor and a pH sensitive $PCO_2$ sensor, respectively, on the surface of the body. FIG. 2 shows a sectional view of typical $PO_2$ non-invasive sensor assembly.

A rod-shaped cathode 5 is disposed in the center, and an anode 7 is mounted about the cathode 5 with intervening glass insulation 6. The ends of the anode contact an electrolyte 9 which is covered by an electrode membrane 8. The peripheral portion of the electrode 7 is covered by a metal heating ring 10 and a skin-heating metal plate 11. An exposed portion of the skin-heating metal plate 11 is made to contact the skin surface when the sensor assembly is attached to the surface of the body. As described above, four sets of electrodes need be attached to the surface of the human body when the above four functions are to be measured simultaneously. When such a large number of electrodes and sensors are required to be attached to a limited surface area of the patient, it often happens that some of the functions must be measured later due to space limitations. In addition, as the number of electrodes or sensors to be attached increases, the number of electric lead wires will naturally increase and cause difficulties in the handling of the electrodes or sensors in an intensive care unit.

SUMMARY OF THE INVENTION

It is the object of the present invention to provide an improved sensor device for measurement of the four above mentioned cardiopulmonary functions which enables simultaneous and continuous measurement of the human body in a non-invasive manner. As previously mentioned, each of the $PO_2$ and $PCO_2$ sensors uses a skin-heating metal plate in order to obtain a sufficient and stable state of vasodilation of the tissues under the surface of the skin. Therefore, the present invention is characterized in that a skin-heating plate is utilized as an electrode for measuring the respiration rate and encardiography, so that the four functions can be determined by means of only two electrode sets or sensors.

DETAILED DESCRIPTION OF THE PREFERRED EMBODIMENT

Figure 1:
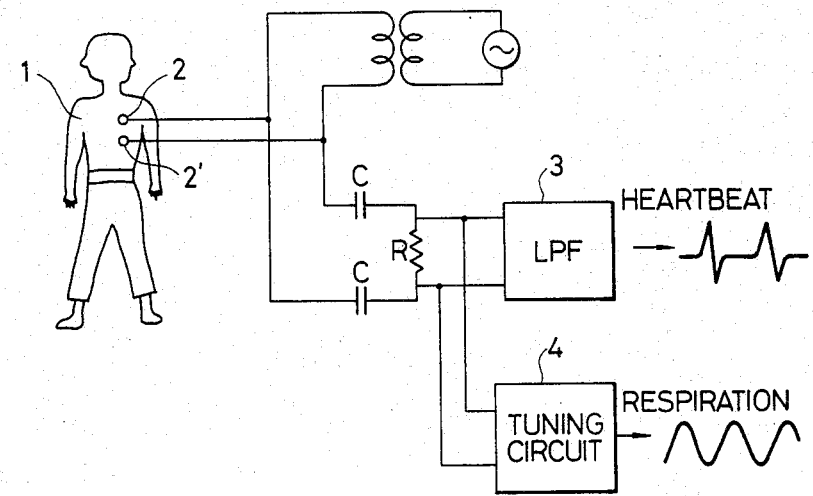
FIG. 1 is a circuit diagram of a device for measuring heartbeat and respiration.
Figure 2:
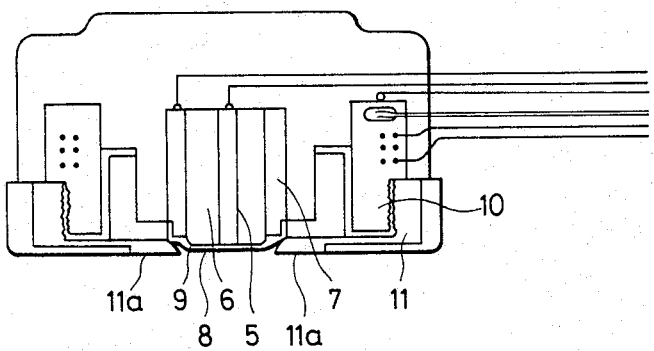
FIG. 2 is a sectional diagram of a preferred embodiment of the present invention.
Figure 3:
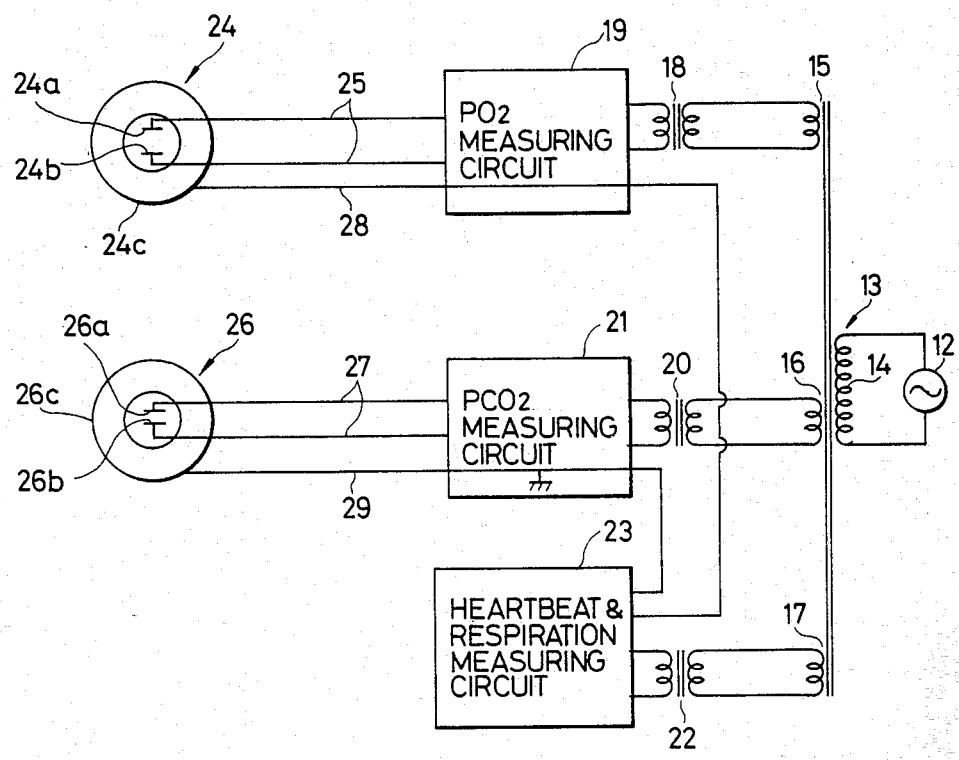
FIG. 3 is a circuit diagram of a preferred embodiment of the present invention.

A preferred embodiment of the present invention will now be described with reference to FIG. 3. In FIG. 3, an AC power source 12 is connected to a primary coil 14 of a transformer 13. Three coils 15, 16 and 17 are wound on the secondary side of the transformer 13. The coil 15 is connected through a transformer 18 to a $PO_2$ measuring circuit 19, the coil 16 is connected through a transformer 20 to a $PCO_2$ measuring circuit 21, and the coil 17 is connected through a transformer 22 to a heartbeat and respiration measuring circuit 23. As the $PO_2$ measuring circuit 19, the $PCO_2$ measuring circuit 21 and the heartbeat and respiration measuring circuit 23, conventional circuits may be used, respectively. Reference numeral 24 designates the $PO_2$ sensor shown in FIG. 2. Electrodes 24a, 24b are connected to the $PO_2$ measuring circuit 19 through lead wires 25. Similarly, electrodes 26a, 26b of the $PCO_2$ sensor 26, which has the same construction as the above mentioned $PO_2$ sensor 24, are connected to the $PCO_2$ measuring circuit 21 through lead wires 27. Rings 24c, 26c, illustrated by circles drawn about the electrodes of the $PO_2$ sensor 24 and the $PCO_2$ sensor 26 are similar to the skin-heating metal plates 11 shown in FIG. 2, and are connected to the heartbeat and respiration measuring circuit 23 through lead wires 28 and 29 respectively. In other words, the rings 24c, 26c serving as skin-heating metal plates also function as the electrodes 2, 2 shown in FIG. 1. There are no particular differences in electrical operation between the rings 24c, 26c and conventional ones.

In conducting measurement using the preferred embodiment, the $PO_2$ sensor 24 and the $PCO_2$ sensor 26 are attached at positions suitable for measuring heartbeat and respiration. $PO_2$ is then measured through the electrodes 24a, 24b while $PCO_2$ is measured through the electrodes 26a, 26b as usual. At the same time, heartbeat and respiration can be measured using the rings 24c, 26c as electrodes. In other words, it becomes possible to conduct the measurement of four parameters simultaneously by attaching only two sensors.

For the lead wires 25, 25 and 28, a three-wire cable can be used, and for the lead wires 27, 27 and 29 a second three-wire cable can be used likewise. The number of cords thus decreases, so that handling is facilitated.

As mentioned above, according to the present invention, it is possible to conduct the measurement of four functions simultaneously using only two sets of electrodes. In addition, the handling of the equipment is facilitated due to the decreased number of electrode or sensor lead wires.

What is claimed is:

1. A sensor device for the measurement of cardio-pulmonary functions, comprising:

first means for the transcutaneous measurement of a blood gas partial pressure, said first means including sensing elements and a heat conducting member having a skin contact surface and surrounding the sensing elements of said first means; and second means for measuring at least one of the heartbeat and respiration rate, said second means including an electrically conducting electrode comprising said heat conducting member.

2. A device as claimed in claim 1, said first means comprising one of a $PO_2$ and $PCO_2$ sensor.

3. A device as claimed in claim 1, said second means including circuit means electrically connected to said heat conducting member for measuring the heartbeat and respiration rate from a signal generated by said heat conducting member.

4. A device as claimed in claim 1, said first means comprising a first measuring circuit and one of a $PO_2$ and $PCO_2$ sensor including as said sensing elements an electrode pair electrically connected to said measuring circuit by a pair of lead wires, and said second means including a second measuring circuit electrically connected to said heat conducting member by a further lead wire for measuring respiration and heartbeat from a signal generated by said heat conducting member.

5. A device as claimed in claim 4, said pair of lead wires and said further lead wire together constituting a three-wire cable extending from said sensor and said heat conducting member to the combination of said first and second measuring circuits.

6. A sensor for the simultaneous and continuous measurement of the cardio-pulmonary functions of the human body, comprising:

(a) an electrode assembly for the transcutaneous measurement of partial gas pressure in arterial blood comprising the following three disassemblably assembled parts:

an electrode part having an anode or reference electrode having a ring-shaped working surface, a cathode or measuring electrode having a working surface inside said anode or reference electrode, and an electrode holder of thermally and electrically insulating material holding said anode or reference electrode and said cathode or measuring electrode apart from one another in insulated relation, a membrane holder part having a blood gas permeable membrane thereon and a membrane holder holding the periphery of said membrane and holding the membrane in spaced relation to the anode and cathode; and a skin heating part having an electrical heater, and a heat conducting metal block to which said heater is heat-conductively connected, said heat conducting metal block having a skin-contact surface and surrounding said anode and cathode;

(b) means for measuring at least one of the respiration rate and heartbeat connected to said skin-contact surface, said surface comprising an electrode of said measuring means.

7. A sensor device for the measurement of cardio-pulmonary functions, comprising:

first means for the transcutaneous measurement of a first blood gas partial pressure, said first means including first sensing elements and a first heat conducting member having a skin contact surface and surrounding said first sensing elements;

second means for the transcutaneous measurement of a second blood gas partial pressure, said second means including second sensing elements and a second heat conducting member having a skin contact surface and surrounding said second sensing elements; and third means for measuring at least one of the heartbeat and respiration rate, said third means including a first electrically conducting electrode comprising said first heat conducting member and a second electrically conducting electrode comprising said second heat conducting member.

* * * * *